United States Patent [19]

Asada et al.

[11] Patent Number: 5,463,548
[45] Date of Patent: Oct. 31, 1995

[54] METHOD AND SYSTEM FOR DIFFERENTIAL DIAGNOSIS BASED ON CLINICAL AND RADIOLOGICAL INFORMATION USING ARTIFICIAL NEURAL NETWORKS

[75] Inventors: Naoki Asada, Higashioji, Japan; Kunio Doi, Hinsdale, Ill.

[73] Assignee: Arch Development Corporation, Chicago, Ill.

[21] Appl. No.: 53,345

[22] Filed: Apr. 28, 1993

Related U.S. Application Data

[63] Continuation of Ser. No. 573,800, Aug. 28, 1990, abandoned.
[51] Int. Cl.$^6$ .................................................. G06F 159/00
[52] U.S. Cl. ..................... 364/413.02; 395/11; 395/21
[58] Field of Search ........................ 364/413.01, 413.02, 364/413.13; 395/11, 20–23

[56] References Cited

U.S. PATENT DOCUMENTS

| | | | |
|---|---|---|---|
| 4,730,259 | 3/1988 | Gallant | 364/43.02 X |
| 4,839,807 | 6/1989 | Doi et al. | 364/413.13 |
| 4,912,647 | 3/1990 | Wood | 364/900 X |
| 4,941,122 | 7/1990 | Weidemann | 364/807 |
| 5,023,045 | 6/1991 | Watanabe et al. | 376/215 |
| 5,046,019 | 9/1991 | Basehore | 364/513 |

OTHER PUBLICATIONS

Journal of Clinical Engineering, vol. 16, No. 6, Dec. 1986, Miller et al. "A Case Study in the Use of an Advanced Expert System Tool or Diagnosis of Cardiovascular Disease", pp. 449–452.
IEEE Int. Conf. on Neural Networks, Jul. 1988, Cat. No. 88CH2632-8, Egbert et al. "Preprocessing of Biomedical Images for Neurocomputer Analysis", pp. 561–568.
IEEE Int. Conf. on Neural Networks, Jul. 1988, Saito et al., "Medical Diagnostic expert System Based on PDP Model", pp. 255–262.
IEEE Int. Conf. on Neural Networks, Jul. 1988, Bounds et al., "A Multi-Layer Perceptron Network for the Diagnosis of Low Back Pain", pp. 481–489.
Neural Networks, vol. 3, No. 5, 1990, "A Comparison of Neural Networks and Other Pattern Recognition Approaches to the Diagnosis of Low Back Disorders", pp. 583–591.
Neurocomputing Applications: Sensor Processing, Control, and Data Analysis, Hecht–Nelson, 1990 Addison–Wesley Pub. Co., pp. 317 to 357.

(List continued on next page.)

Primary Examiner—David M. Huntley
Attorney, Agent, or Firm—Oblon, Spivak, McClelland, Maier, & Neustadt

[57] ABSTRACT

A method and system for computer-aided differential diagnosis of diseases, and in particular, computer-aided differential diagnosis using neural networks. A first embodiment of the neural network distinguishes between a plurality of interstitial lung diseases on the basis of inputted clinical parameters and radiographic information. A second embodiment distinguishes between malignant and benign mammographic cases based upon similar inputted clinical and radiographic information. The neural networks were first trained using a hypothetical data base made up of hypothetical cases for each of the interstitial lung diseases and for malignant and benign cases. The performance of the neural network was evaluated using receiver operating characteristics (ROC) analysis. The decision performance of the neural network was compared to experienced radiologists and achieved a high performance comparable to that of the experienced radiologists. The neural network according to the invention can be made up of a single network or a plurality of successive or parallel networks. The neural network according to the invention can also be interfaced to a computer which provides computerized automated lung texture analysis to supply radiographic input data in an objective and automated manner.

3 Claims, 13 Drawing Sheets

OTHER PUBLICATIONS

INNC 90 Paris Conference, 9–13 Jul. 1990, Anthony et al., "The use of neural networks in classifying lung scintigrams" (abstract only).

Radiology, vol. 177, No. 3, Dec. 1990, Asada et al., "Potential Usefulness of an Artificial Network for Differential Diagnosis of Interstitial Lung diseases" (abstract only).

Conference: Computer Assisted Radiology: Proceedings of the Int. Symposium CAR '91, Jul. 1991, Penedo, "A multi–layered neural network for the recognition of lung nodules on digital chest radiographs" (abstract only).

Conference: The 13th Annual symposium on computer Application in Medical Care, Cat. No. 89tH0286–5, Nov. 1989, Meistrell et al., "Evaluation of neural network performance by receiver operating characteristic analysis" (abstract only).

Am J Clin Pathol, 1991, Dawson et al., "Nuclear Grading of Breast Carcinoma . . . " (abstract only).

Neurol Networks, vol. 3, No. 5, 1990, Silverman, "Image Processing and Pattern Recognition in Ultrasonograms by Backpropagation" (abstract only).

Conference: scientific assembly annual meeting of the radiological society of North America, Chicago, 1987, Oldham et al,. "Neural Network Recognition of Mammographic Lesions" (abstract only).

Conference: Proceedings of the Annual Int. Conf. of the IEEE Eng. in Medicine and Biology Society, Cat. No. 89CH2770–6, 1989, Cohen et al., "Combination of a neural network model and a rule–based expert system to determine efficacy of medical testing procedures" (abstract only).

CLINICAL INFORMATION
- AGE
- SEX
- DURATION OF SYMPTOMS
- SEVERITY OF SYMPTOMS
- TEMPERATURE
- IMMUNE STATUS

RADIOGRAPHIC FINDINGS
- RU (RIGHT UPPER)
- RM (RIGHT MIDDLE)
- RL (RIGHT LOWER)
- LU (LEFT UPPER)
- LM (LEFT MIDDLE)
- LL (LEFT LOWER)
- HOMOGENEITY
- FINENESS/COARSENESS
- NODULARITY
- SEPTAL LINES
- HONEYCOMBING
- LYMPHADENOPATHY
- PLEURAL EFFUSIONS
- HEART SIZE

INTERSTITIAL LUNG DISEASES
- SARCOIDOSIS
- MILIARY TUBERCULOSIS
- LYMPHANGITIC METASTATIC TUMOR
- INTERSTITIAL PULMONARY EDEMA
- SILICOSIS
- SCLERODERMA
- PNEUMOCYSTIS PNEUMONIA
- EOSINOPHILIC GRANULOMA
- USUAL INTERSTITIAL PNEUMONITIS

*FIG. 2*

Mammography Neural Network Data Sheet
Image Case Number ____
Dr. _____ Date: ____
Note: ratings are 0 - 10

I. Clinical data
 A. Patient age (20-100) ___
 B. Family history of cancer ____
 C. Palpable abnormality ____
 D. Previous biopsy results ____

II. Density related features
 A. Existence of abnormal density
  1. asymmetry relative to opposite side ____
  2. correlation of positions on 2 views ____
  3. detectable boundary ____
  4. opacity relative to similarly sized image features ____
  5. multiplicity of density ____

If A.1 - 5 = 0, go to Part III

B. Shape of density
  1. linear to spherical ____
  2. geometrical to diffuse ____
  3. existence of satellite lesions ____
 C. Size of density
  1. approximate mean diameter to ____
 D. Margin of density
  1. complete to inseparable from surround ____
  2. well-defined to indistinct ____
  3. presence of halo sign ____
 E. Margin spiculation
  1. number of spiculations ____
  2. length of spiculations ____
  3. difference between spicules and local linear features ____
 F. Pattern of density
  1. uniformity of density of mass ____
  2. presence of well-defined lucencies ____
  3. opacity relative to size ____

III. Microcalcification-related features
 A. Number of microcalcifications
  1. number of microcalcifications in cluster ____

If A.1 = 0, go to Part IV 2. presence of microcalcifications elsewhere in breast ____
 B. Shape of microcalcifications
  1. rounded to irregular ____
  2. presence of linear microcalcifications ____
  3. presence of branched calcifications ____

C. Uniformity of microcalcifications
  1. uniformity in size ____
  2. uniformity in shape ____
  3. uniformity in density ____
 D. Distribution of microcalcifications
  1. diffuseness of cluster ____
  2. shape of cluster, geometric to irregular ____
  3. radiation of microcalcifications along ducts ____
 E. Presence of macrocalcifications
  1. associated with microcalcifications ____
  2. macrocalcifications elsewhere in breast ____

IV. Secondary related features
 A. Parenchymal distortion
  1. subtlety of distortion ____

If A.1 = 0, go to Part IV. B 2. distortion definable on two views ____
  3. presence of similar patterns elsewhere ____
 B. Skin thickening
  1. degree of skin thickening ____

If B.1 = 0, go to Part V 2. association with primary suspicious abnormality ____

V. Comparison with previous studies
 A. Existence of previous study ____

If A. = 0, go to Part VI

B. Comparability of previous study ____
 C. Existence of abnormality on earlier study ____

VI. Correlation with clinical findings

If No palpable abnorm. go to VI.C

A. Correlation between location of clinical finding and radiographic abnormality ____
 B. Correlation between size or extent of clinical finding and radiographic abnormality ____
 C. Level of suspicion due to clinical finding ____

If No previous biopsy, go to Part VII
 D. Location relative to previous biopsy ____

VII. Diagnosis (check one)
  Malignant ___ or Benign ___
VIII. Course of Action (check one)
  Biopsy ___ , Follow-up ___ or
  Return to screening ___

FIG. 12

METHOD AND SYSTEM FOR DIFFERENTIAL DIAGNOSIS BASED ON CLINICAL AND RADIOLOGICAL INFORMATION USING ARTIFICIAL NEURAL NETWORKS

The U.S. Government has a paid-up license in this invention and the right and limited circumstances to require the patent owner to license others on reasonable terms as provided for by the terms of USPHS Grant Nos. CA24804, CA44926 and CA47043 from the National Institute of Health. This application is a Continuation of application Ser. No. 07/573,800, filed on Aug. 28, 1990, now abandoned.

The present invention is related to U.S. Pat. No. 4,839,807 granted to Doi et al and U.S. Pat. No. 4,851,984 granted to Doi et al, which are herein incorporated by reference.

BACKGROUND OF THE INVENTION

1. Field of the Invention

The present invention relates to a method and system for computer-aided differential diagnosis of diseases, and in particular, computer-aided differential diagnosis using neural networks.

2. Discussion of the Background

Computer-aided differential diagnosis of diseases is an important subject in radiology. However, it is difficult to distinguish accurately between many diseases that can produce similar or even identical radiographic interstitial patterns. In such cases, a specific diagnosis can only be made by taking into consideration the multiple relevant clinical aspects of the case, i.e., age, sex, symptoms, etc., together with details of the radiographic findings. Thus, differential diagnosis of diseases lends itself to computer automation which can provide assistance to less expert observers of radiographic patterns, to bring the decision performance of these less expert observers to a level closer to that of experienced radiologists. However, computer-aided differential diagnosis of diseases has not gained wide acceptance due to the multiple clinical aspects of a case.

A powerful tool for use in solving problems involving pattern recognition and classification is an artificial neural network having a layered structure and applied with a supervised-learning procedure such as the back-propagating error correction algorithm as disclosed by Rumelhart et al "Parallel distributed processing" "Explorations in the Microstructure of Cognition" Cambridge: MIT Press (1986), Grossberg " Neural Network and Neural Intelligence" Cambridge: MIT Press (1988), and Eckmiller et al "Neural Computers" Berlin: Springer-Verlag (1989), which are herein incorporated by reference. Artificial neural networks consist of a number of neuron-like elements (units) and connections between them, and can be implemented by hardware and/or software. The units of the neural network are categorized into three types of different groups (layers) according to their functions as shown in FIG. 1. A first layer (input layer) is assigned to accepting a set of data representing an input pattern, a second layer (output layer) is assigned to provide a set of data representing an output pattern, and an arbitrary number of intermediate layers (hidden layers) convert the input pattern to the output pattern. Since the number of units in each layer is determined arbitrarily, the input layer and the output layer include sufficient numbers of units to represent the input patterns and output patterns, respectively, of a problem to be solved. For example, a neural network which is designed to distinguish between 9 types of diseases on the basis of 20 items of clinical information, should have 20 input units and 9 output units. However, the optimum number of hidden layers and associated units needs to be determined empirically.

Briefly, the principle of neural network can be explained in the following manner. Input data, which are represented by numbers ranging from 0 to 1, are supplied to input units of the neural network. Next, the output data are provided from output units through two successive nonlinear calculations (in a case of one hidden layer) in the hidden and output layers. The calculation at each unit in the layer, which is illustrated schematically in FIG. 2, excluding the input units, includes a weighted summation of all entry numbers, an addition of certain offset terms and a conversion into a number ranging from 0 to 1 using a sigmoid-shape function such as a logistic function. In FIG. 2, units labelled $O_1$ to $O_n$ represent input or hidden units, $W_1$ through $W_n$ represent the weighting factors assigned to each respective output from these input or hidden units, and I represents the summation of the outputs multiplied by the respective weighting factors. An output O is calculated using the logistic-function equation given where $\theta$ represents an offset value for the input I. The weighting factors and offset values are internal parameters of the neural network which are determined for a given set of input and output data.

Two different basic processes are involved in the neural network, namely, a training process and a testing process. The neural network is trained by the back-propagation algorithm using pairs of training input data and desired output data, as given by Rumelhart et al, Ibid, pp. 318–362. The internal parameters of the neural network are adjusted in order to minimize the difference between the actual outputs of the neural network and the desired outputs. By iteration of this procedure in a random sequence for the same set of input and output data, the neural network learns a relationship between the training input data and the desired output data. Once trained sufficiently, the neural network can distinguish different input data according to its learning experience. To date, the neural network approach has not been applied to the computer-aided differential diagnosis of interstitial diseases.

SUMMARY OF THE INVENTION

Accordingly, it is an object of the present invention to provide a novel method and system for the computer-aided differential diagnosis of diseases including a neural network.

It is another object of the present invention to provide a new and improved method and system for the computer-aided differential diagnosis of diseases including a neural network which improves the diagnosis decision performance of radiologists.

These and other objects are achieved according to the invention by providing a new and improved method and system for diagnosis of diseases, based upon the input of clinical parameters and radiographic descriptors into a neural network. For the case of interstitial lung diseases, the clinical parameters selected are the patient's age, sex, duration of symptoms, severity of symptoms, temperature and immune status. The radiographic descriptors include information regarding the distribution of infiltrates in the lungs and information relating to details of the infiltrate. The clinical parameters and radiographic descriptors are converted into numerical expressions and then transformed into a number between 0 and 1. These transformed expressions are input into a neural network having a plurality of input units and a plurality of output units. The neural network diagnoses one of the plurality of interstitial lung diseases based upon the transformed numerical expressions inputted thereto. The system and method of the present invention allows less expert observers, i.e., radiology residents or clinicians, to improve their differential diagnosis decision performance to a level closer to that of experienced radiologists.

In another embodiment, the method of the present invention is applied to mammographic diagnosis of breast cancer to distinguish between benign and malignant cases. Clinical parameters and radiographic descriptors are transformed into numerical expressions and input into a neural network which outputs a diagnosis based upon the input expressions.

It is important to note that neural networks are not effective for solving problems in all applications of radiological diagnosis. Radiological diagnoses are often made based on findings of abnormal patterns which are commonly closely related to a disease, diseases or a state. For example, the detection of lung cancer, cardiomegaly, and pneumothorax is primarily due to the findings of lung nodules, enlargement of cardiac outline and subtle curved line structure, respectively. Radiological diagnosis on ultrasound images, which are well known to be of poor quality due to low resolution, high noise level and artifacts, is made by highly trained radiologists able to distinguish between normal and abnormal patterns. For this task, correct recognition of certain image patterns by radiologists is the most important element for achieving accurate diagnosis. This example indicates that the application of neural networks will not be helpful for decision making in many radiological diagnosis situations. Therefore, prior to the present invention, the utility and effectiveness of neural networks in differential diagnosis was not considered and unknown, and in particular with respect to differential diagnosis of interstitial lung diseases. The present invention is a novel use of neural networks in the field of differential diagnosis, which provides an effective and accurate differential diagnosis.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 is a schematic illustration of the calculation in a unit of an artificial neural network according to the prior art;

FIG. 12 is a data sheet used in mammographic diagnosis including clinical parameters and mammographic descriptors.

DESCRIPTION OF THE PREFERRED EMBODIMENTS

The present invention relates to the differential diagnosis of diseases, and the following discussion directed to differential diagnosis of interstitial lung diseases is provided for example only, and it is understood that the present invention is not limited thereto.

Figure 1:
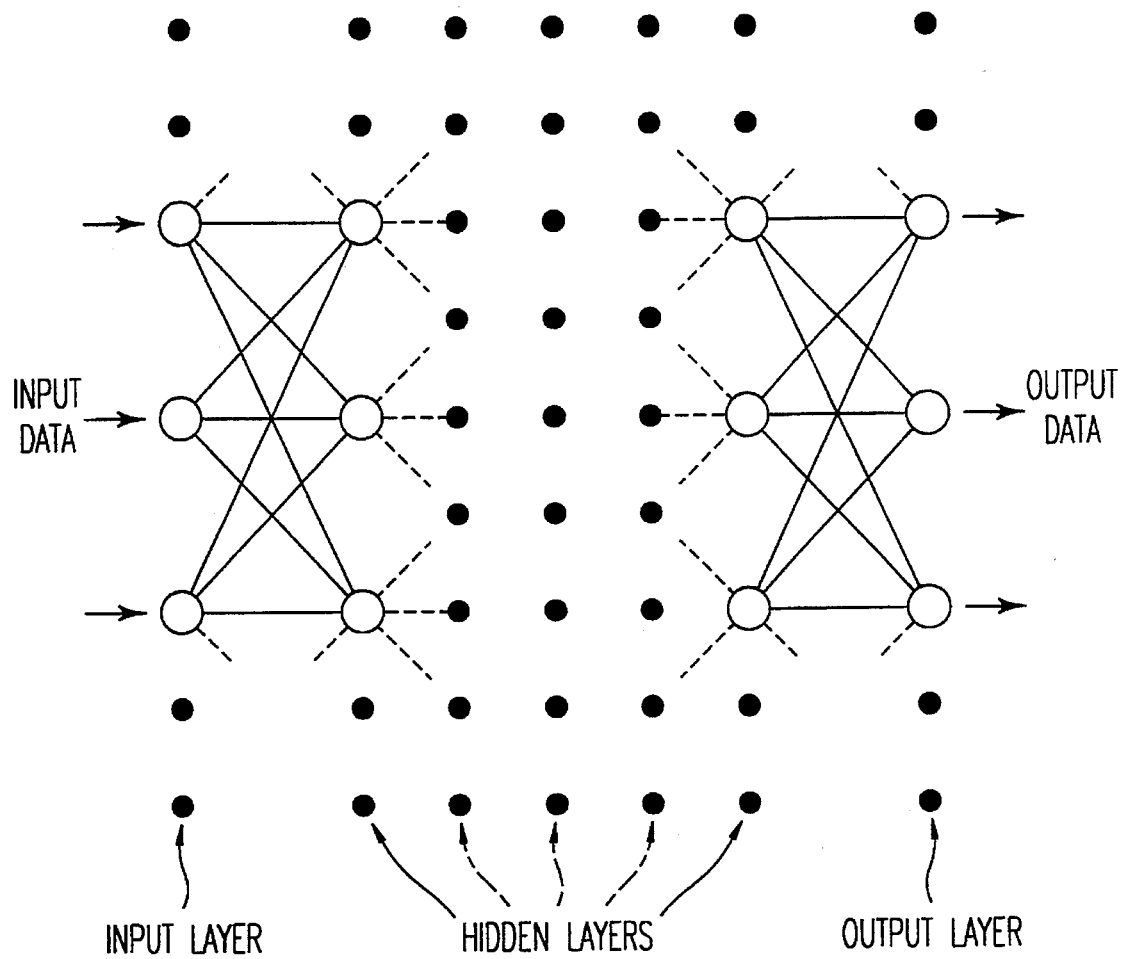
FIG. 1 is a diagram of the basic structure of an artificial neural network having a layered structure according to the prior art.
Figure 3:
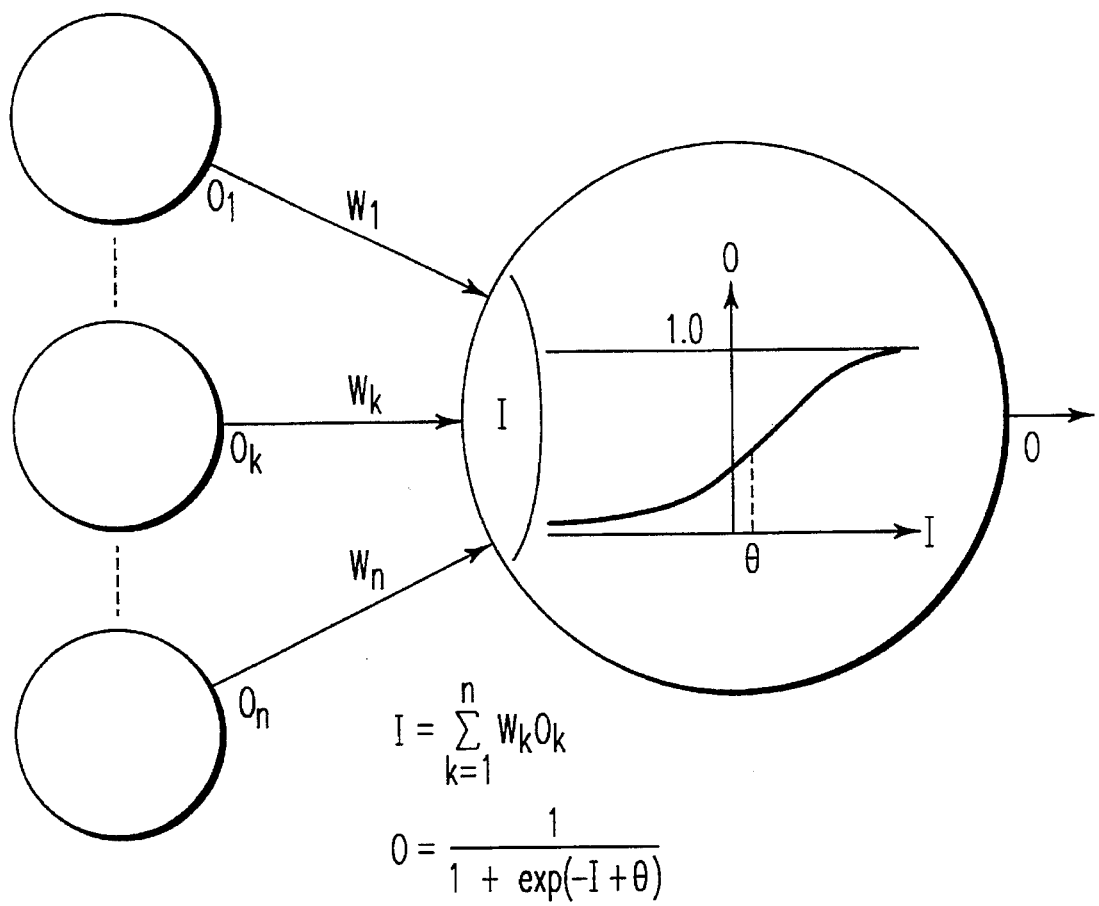
FIG. 3 is a diagram of a neural network according to the present invention, including 20 inputs units, 9 output units and 1 hidden layer with 2 units.

Referring now to the drawings, and more particularly to FIG. 3 thereof, 9 types of interstitial lung diseases for differential diagnosis were identified by chest radiologists, namely, sarcoidosis, miliary tuberculosis, lymphangitic metastatic tumor, interstitial pulmonary edema, silicosis, scleroderma, pneumocystis pneumonia, eosinophilic granuloma and usual interstitial pneumonitis (UIP). Also identified were 6 key clinical parameters which are the patient's age, sex, duration of symptoms, severity of symptoms, temperature and immune status, and 14 radiographic descriptors which include 6 items regarding distribution of infiltrates in 6 divisions (upper, mid and lower zones of right and left lungs), 6 items relating to details of the infiltrate (homogeneity, fineness/coarseness, nodularity, septal lines and honeycombing) and 3 additional radiographic parameters (lymphadenopathy, pleural effusions and heart size).

Thus, the neural network was designed to include 20 input units (6 clinical parameters and 14 radiographic descriptors) and 9 output units (9 interstitial lung diseases). FIG. 3 shows the basic structure of the neural network according to a first embodiment of the present invention. The intermediate layer, which is called the hidden layer, plays an important role in converting the input patterns to output patterns. This embodiment contains one hidden layer with two units.

However, the number of hidden layers and the number of associated units can be changed in accordance with the desired structure and performance of the resulting network.

Hypothetical Database

In order to evaluate the decision performance of the neural network, a database was created for the training and testing processes. Two chest radiologists independently selected clinical data and radiographic findings for 10 hypothetical examples of each of the 9 diseases for a total of 90 cases. All input data for the neural network can be converted into numbers ranging from 0 to 1 using a linear or non-linear transformation. For example, the body temperature, which ranged from 37° C. to 41° C., was converted linearly into a number between 0 and 1. Radiographic descriptors were initially scored on a subjective scale from 0 to 10, and then normalized to the range from 0 to 1. It should be noted that any kind of description even including fuzzy descriptive expressions such as "very large", "large", "probably", "small" and "very small" can be converted into a number ranging from 0 to 1 using a membership function which can be defined appropriately based on the techniques used in fuzzy theory. Dubois et al "Fuzzy Set and Systems: Theory and Applications", Academic Press (1980), and Zimmermann "Fuzzy Set Theory—and its Applications", Kluwer-Nijhoff Publishing (1985), whose disclosures are herein incorporated by reference.

As stated earlier, a neural network with a layered structure has the ability to learn the relationship between input data and output data from examples presented repeatedly. In other words, the discrimination criteria produced in the neural network depend on the number of variety of the training examples used. Therefore, the training database should be created ideally by selecting appropriate examples that represent a wide distribution of all potential cases. However, it is very time-consuming to create an appropriate database by collecting actual patient cases prospectively, and the relevant clinical information was not consistently available in teaching file cases.

Two chest radiologists selected 10 cases for each of the 9 diseases on the basis of textbooks descriptions and their own experience. Thus, hypothetical data was used for training the neural network. The hypothetical database approach has an advantage in that varied distributions of all diseases can be represented to some extent with a relatively small number of total cases. A neural network trained with hypothetical data needs to be validated by testing with a large number of actual cases, prior to clinical application.

The neural network according to the present invention was examined with 5 actual cases which fulfilled the criterion of having an interstitial infiltrate due to one of the nine selected diseases. All of these resulted in correct decisions. Further studies will determine the ultimate accuracy achievable in clinical situations, and also identify the need for modification of the database.

However, it is important to note that the neural network according to the present invention can be retrained by adding new data to the existing training cases. Thus, if the neural network fails to yield a correct diagnosis on some actual cases, these new data can be incorporated into the database along with the correct diagnosis so that very similar cases, which may be encountered subsequently, will be correctly identified.

Optimal Parameters

A jackknife method was employed for the evaluation of the neural network, that is, half of the cases, which were selected randomly from the database, were used for training, and the remaining half for testing. By random selection of cases, 10 different pairs of training and testing data sets were prepared. The outputs of the testing process were analyzed by determining true-positive and false-positive decisions, which were used for plotting the ordinate and abscissa, respectively, of ROC (receiver operating characteristics) curves.

The ROC curve is known at present as the most reliable diagram which indicates the performance of detectors (or observers) in distinguishing between two possible states, such as normal and abnormal, for lungs. The ROC curve is generally a plot of the relationship between the true-positive fraction, i.e., the fraction of correct classifications (or detections) of the abnormal lung as abnormal and the false-positive fraction, i.e., the fraction of incorrect classifications (or detections) of the normal lung as abnormal. This relationship is expressed by a curve instead of a point because these fractions can change depending on the threshold level used, as disclosed in U.S. Pat. No. 4,839,807.

Using average ROC curves obtained from 10 different data sets, the optimal parameters for the neural network according to the first embodiment were determined in terms of the number of hidden units, the number of hidden layers, and the number of learning iterations. The effect of the number of hidden units was examined by changing the number from 1 to 20 with the condition of one hidden layer and 200 learning iterations. In the same manner, the number of hidden layers was changed from 1 to 3 with 6 hidden units per layer and 200 learning iterations. The number of learning iterations was varied from 1 to 1000 with 1 hidden layer and 6 hidden units. The learning iterations were counted on every entry of a complete set of different training data. In addition, the effect of some other technical parameters such as learning rate, momentum factor of weight change and seed for random number generation were examined.

For training the neural network, 10 hypothetical cases for each disease were applied. However, as the actual cases are accumulated, the number of total cases collected for each disease may not be equal. In fact, it is likely that the number of training cases for rare diseases can be significantly smaller than those for common diseases. This insufficient number of training cases for a certain disease will cause a decrease in the sensitivity of detecting a specific disease. This problem is related to the prevalence (or frequency of occurrence) of diseases and can be solved to some extent by increasing the number of entries of the same training case for the rare disease. For example, if a common disease and a rare disease may have 100 cases and 10 cases respectively, then the 100 cases of the common disease may be entered for 200 iterations, but the 10 cases of the rare disease may be entered for 2000 iterations. Therefore, the total numbers of data entries for training the neural network for diseases having different prevalences, can be equalized.

A more complete discussion of the learning procedure used in training the neural network according to the first embodiment of the present invention, i.e., the back-propagating method, is described in the Rumelhart et al references and is omitted here for brevity.

Figure 4:
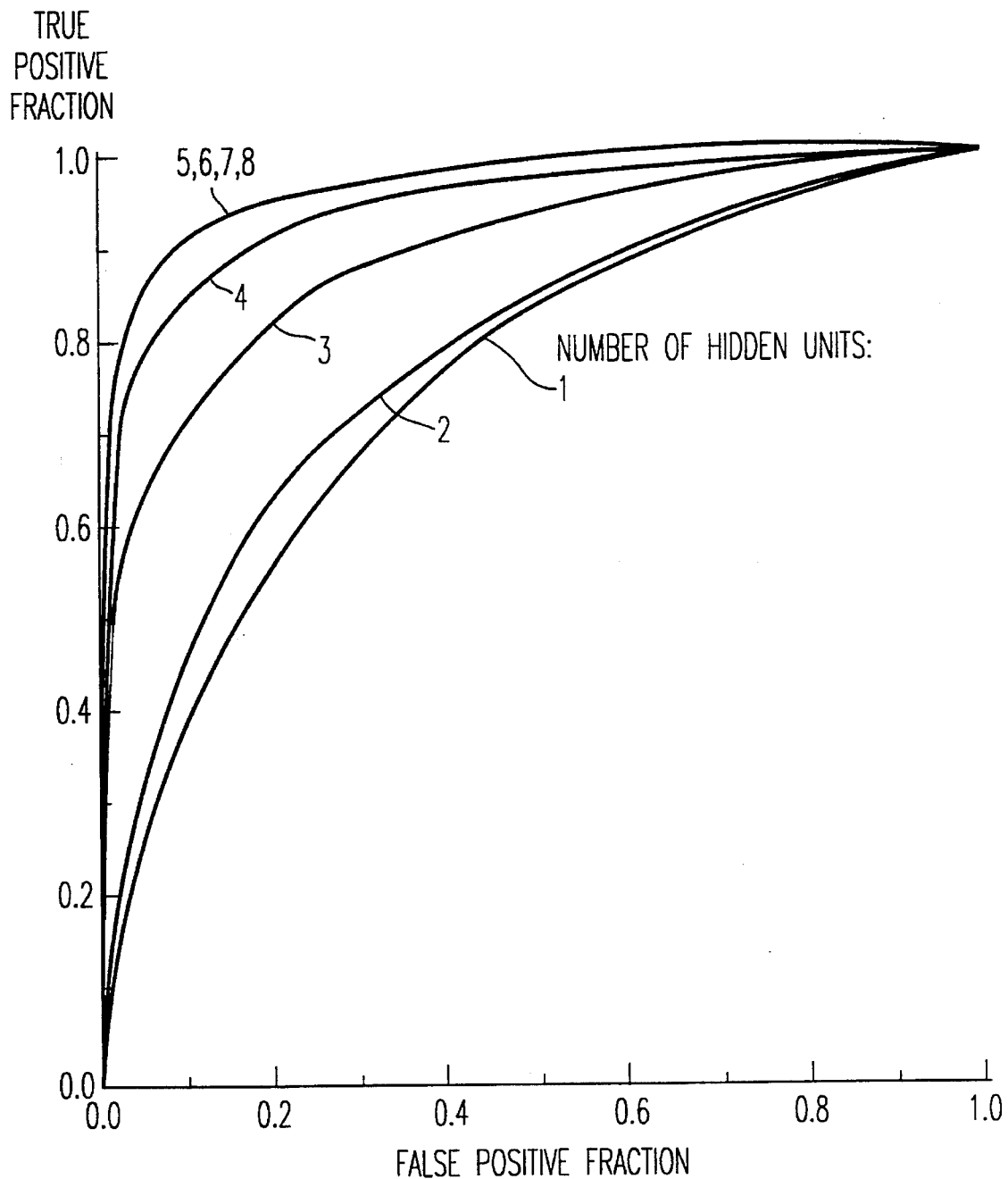
FIG. 4 is a graphical illustration of the effect of the number of hidden units on ROC curves of a neural network according to the present invention, wherein the number of hidden units ranges from 1 to 8 with the condition of 1 hidden layer and 200 learning iterations.
Figure 5:
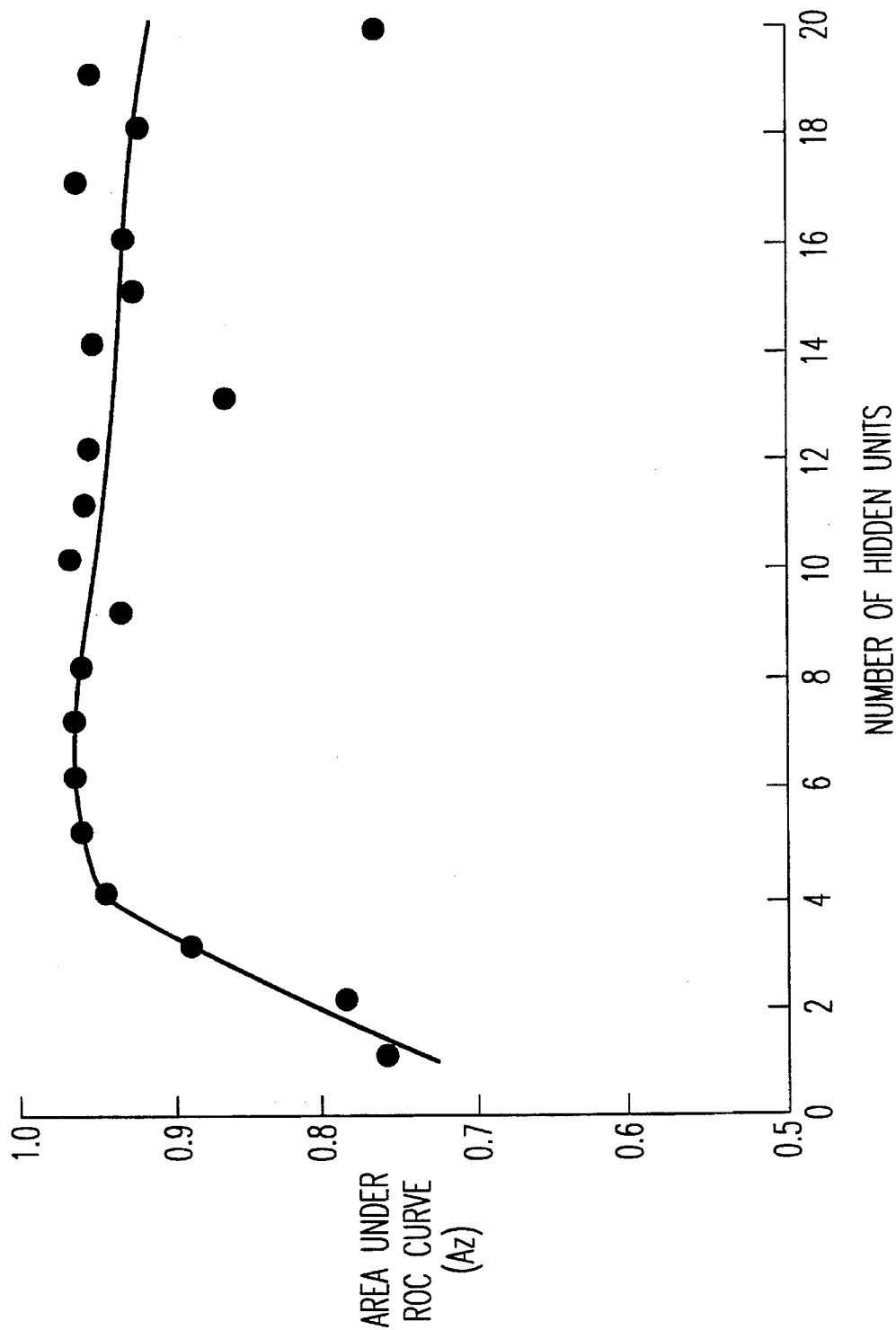
FIG. 5 is a graphical illustration of the effect of the number of hidden units on the area under the ROC curves of a neural network according to the present invention, wherein the number of hidden units ranges from 1 to 20 with a condition of 1 hidden layer and 200 learning iterations.

FIG. 4 illustrates the ROC curves showing the effect of the number of hidden units on the performance of the neural network according to the first embodiment of the present invention. The ROC curve improves as the number of hidden units increases up to 8. However, the relationship between the area under the ROC curve (Az) and the number of hidden units, as shown in FIG. 5, indicates that more than 8 hidden units does not significantly improve the ROC curves, compared with the condition of 1 hidden layer and 200 learning iterations. In order to determine the optimal number of hidden units, the effect of a number of hidden units to distinguish completely all 90 cases of the database which were used for training first and then testing of the neural network was examined. Note that this was not the previously mentioned jack-knife test, but rather a verification test for consistency of the neural network according to the first embodiment of the present invention. Based on these curves, the minimum number of hidden units was determined as 6.

Figure 6:
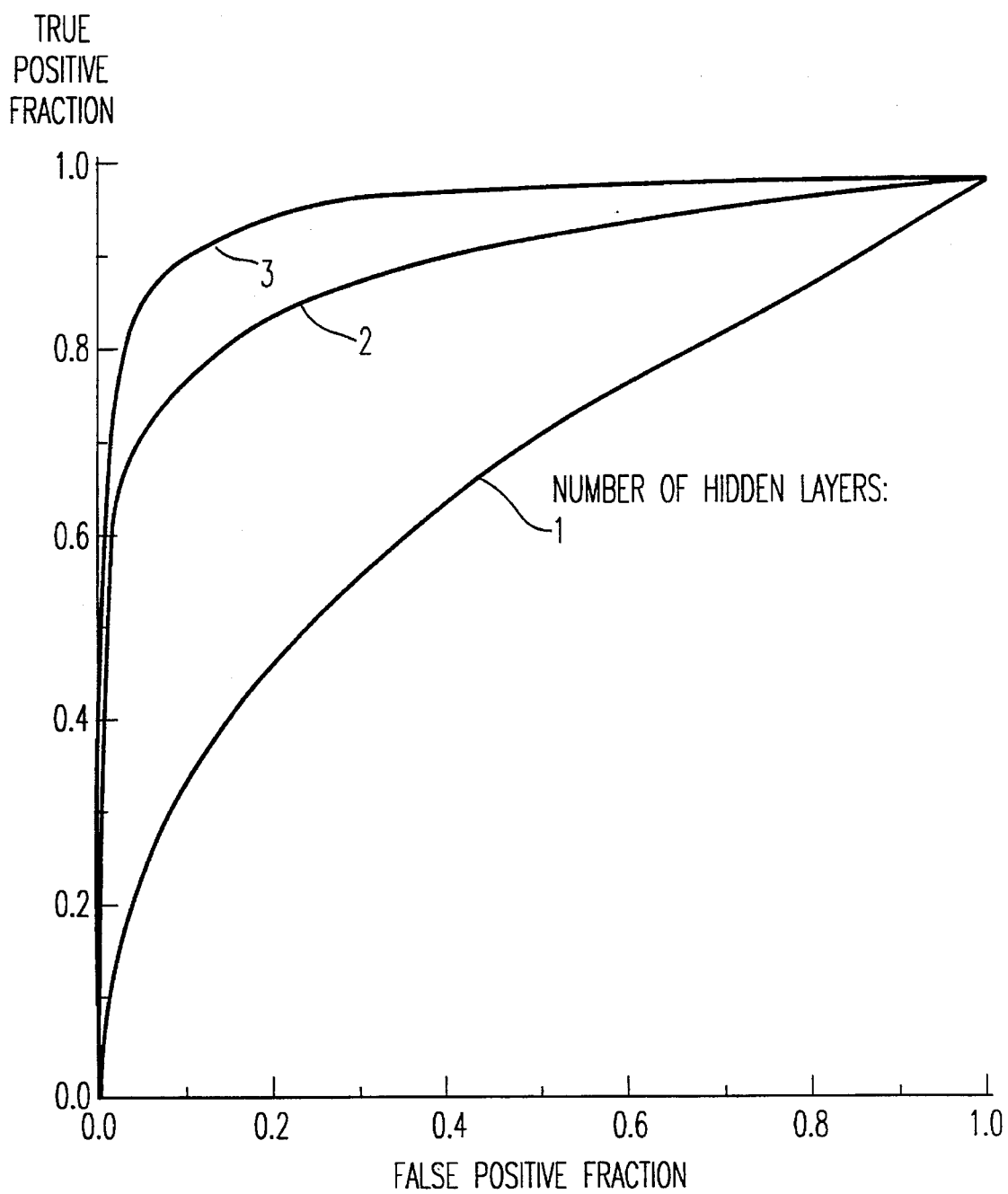
FIG. 6 is a graphical illustration of the effect of the number of hidden layers on ROC curves of a neural network according to the present invention, wherein the number of hidden layers ranges from 1 to 3 with a condition of 6 hidden units per layer and 200 learning iterations.

FIG. 6 illustrates the ROC curves obtained with differing numbers of hidden layers. It is to be observed that the ROC curves deteriorated as the number of hidden layers increases. One hidden layer provides the highest ROC curve under the condition of 6 hidden units per layer and 200 learning iterations. As the learning iterations increase to 1000, virtually the same ROC curves are obtained as in the case of 200 learning iterations with no appreciable improvement. Accordingly, the neural network according to the first embodiment of the present invention includes one hidden layer.

Figure 7:
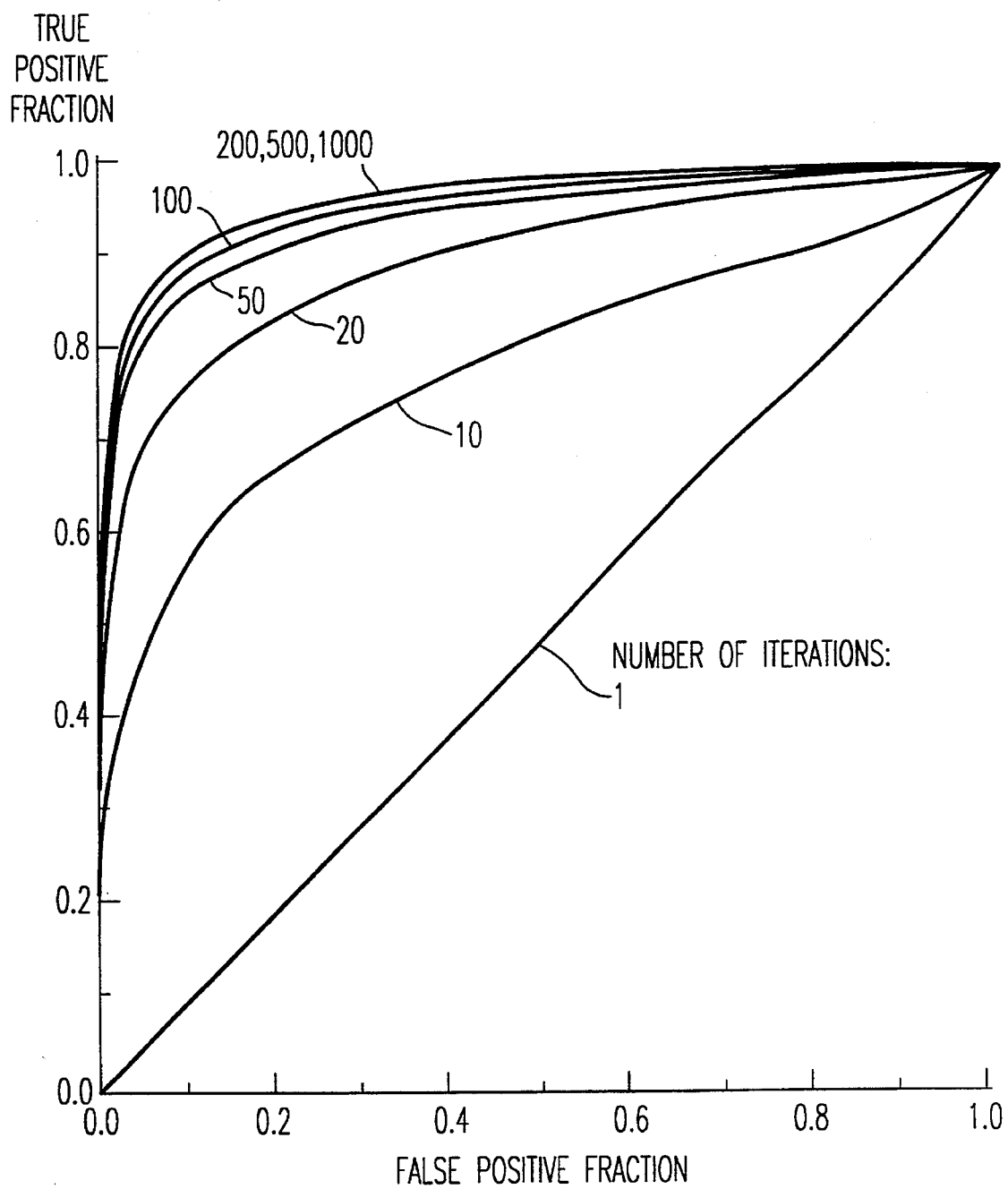
FIG. 7 is a graphical illustration of the effect of learning iterations on ROC curves of a neural network according to the present invention, wherein the number of learning iterations ranges from 1 to 1,000 with the condition of 1 hidden layer and 6 hidden units.

The ROC curves obtained with different numbers of learning iterations are shown in FIG. 7. Improvement in the ROC curves is observed as the number of learning iterations increases. The highest ROC curve is obtained for 200 or more learning iterations. Thus, 200 learning iterations is a sufficient number for training the neural network according to the first embodiment of the present invention.

Accordingly, the neural network according to the first embodiment of the present invention includes one hidden layer having 6 units and was trained with 200 learning iterations. A discussion of the selection and learning processes is also described in Asada et al, "Neural Network Approach for Differential Diagnosis of Interstitial Lung Diseases", Proc. SPIE Medical Imaging IV (1990), which is herein incorporated by reference.

Consistency Verification Test

Prior to performing the decision performance test, a consistency test of the neural network was performed. The neural network was trained in all cases in the database, and then tested by an average case of the 10 cases for each of the 9 diseases in the database. The average input values to the neural network and the corresponding output values from the neural network are shown in Tables 1 and 2, respectively. Table 1 represents the average input data estimated from 10 cases for each of the 9 diseases in the database. Table 2 provides output data of the neural network according to the first embodiment of the present invention for a given set of the average input data given in Table 1. In Table 2, the 9 rows correspond to the 9 output units and the 9 columns correspond to the 9 columns of Table 1. The large output values, such as 0.9 along the diagonal in Table 2, indicate that the neural network recognizes the input data as the

| | 9 types of interstitial lung diseases | | | | | | | | |
|---|---|---|---|---|---|---|---|---|---|
| Input unit name | sarcoidosis | miliary tuberculosis | metastatic tumor | pulmonary edema | silicosis | scleroderma | pneumocystis pneumonia | eosinophilic granuloma | UIP |
| age | 32 | 53 | 59 | 60 | 67 | 40 | 37 | 34 | 54 |
| sex* | 0 | 0 | 1 | 1 | 1 | 0 | 1 | 1 | 1 |
| duration of symptoms** | 2 | 1 | 3 | 1 | 7 | 5 | 1 | 3 | 5 |
| severity of symptoms | 1 | 8 | 5 | 5 | 3 | 3 | 8 | 1 | 4 |
| temperature | 37.6 | 39.9 | 37.6 | 37.2 | 37.1 | 37.4 | 39.7 | 37.4 | 37.1 |
| immune status*** | 0 | 0 | 0 | 0 | 0 | 0 | 1 | 0 | 0 |
| RU | 4 | 4 | 3 | 3 | 7 | 1 | 4 | 6 | 2 |
| RM | 3 | 4 | 4 | 5 | 5 | 3 | 4 | 4 | 3 |
| RL | 2 | 4 | 5 | 5 | 3 | 6 | 4 | 1 | 5 |
| LU | 4 | 4 | 3 | 3 | 7 | 1 | 4 | 6 | 2 |
| LM | 3 | 4 | 4 | 5 | 5 | 3 | 4 | 3 | 3 |
| LL | 2 | 5 | 6 | 6 | 3 | 6 | 4 | 1 | 5 |
| homogeneity | 6 | 8 | 6 | 7 | 6 | 7 | 9 | 8 | 8 |
| fineness/coarseness | 3 | 2 | 6 | 4 | 5 | 3 | 2 | 5 | 4 |
| nodularity | 3 | 9 | 6 | 1 | 7 | 1 | 0 | 5 | 2 |
| septal lines | 0 | 0 | 4 | 6 | 1 | 1 | 0 | 0 | 1 |
| honeycombing | 1 | 0 | 0 | 0 | 3 | 2 | 0 | 7 | 5 |
| lymphadenopathy | 6 | 0 | 4 | 0 | 3 | 0 | 1 | 0 | 0 |
| pleural effusions | 0 | 2 | 4 | 4 | 0 | 0 | 0 | 0 | 0 |
| heart size | 2 | 1 | 2 | 4 | 2 | 1 | 1 | 1 | 1 |

*0 = female, 1 = male
**month (unit)
***0 = normal, 1 = suppressed

| | 9 types of interstitial lung diseases (correct diagnosis) | | | | | | | | |
|---|---|---|---|---|---|---|---|---|---|
| Output unit name | sarcoidosis | miliary tuberculosis | metastatic tumor | pulmonary edema | silicosis | scleroderma | pneumocystis pneumonia | eosinophilic granuloma | UIP |
| sarcoidosis | 0.99 | 0.00 | 0.00 | 0.00 | 0.02 | 0.00 | 0.00 | 0.00 | 0.00 |
| miliary tuberculosis | 0.00 | 0.99 | 0.01 | 0.00 | 0.01 | 0.00 | 0.00 | 0.00 | 0.00 |
| metastatic tumor | 0.00 | 0.00 | 0.98 | 0.01 | 0.01 | 0.00 | 0.00 | 0.00 | 0.00 |
| pulmonary odema | 0.00 | 0.00 | 0.01 | 0.98 | 0.00 | 0.00 | 0.00 | 0.00 | 0.01 |

-continued

| | 9 types of interstitial lung diseases (correct diagnosis) | | | | | | | | |
| --- | --- | --- | --- | --- | --- | --- | --- | --- | --- |
| Output unit name | sarcoidosis | miliary tuberculosis | metastatic tumor | pulmonary edema | silicosis | scleroderma | pneumocystis pneumonia | eosinophilic granuloma | UIP |
| silicosis | 0.00 | 0.00 | 0.01 | 0.00 | 0.98 | 0.00 | 0.00 | 0.01 | 0.01 |
| scleroderma | 0.00 | 0.00 | 0.00 | 0.01 | 0.00 | 0.97 | 0.01 | 0.00 | 0.00 |
| pneumocystis pneumonia | 0.00 | 0.00 | 0.00 | 0.01 | 0.00 | 0.01 | 0.99 | 0.00 | 0.00 |
| eosinophnic granuloma | 0.00 | 0.00 | 0.00 | 0.00 | 0.01 | 0.00 | 0.00 | 0.99 | 0.00 |
| UIP | 0.00 | 0.00 | 0.00 | 0.01 | 0.01 | 0.10 | 0.00 | 0.00 | 0.99 | disease shown on the same column with high probability. In addition, the small output values, such as 0.01, 0.02 and 0.1 in other locations, suggests that the probability of false-positive decisions is very low. Therefore, Table 2 demonstrates the consistency of the neural network, which identified each of the 9 diseases with high probability.

Decision Performance

The decision performance of the neural network was compared with those of chest radiologists and of senior radiology residents. Three chest radiologists and three senior residents were tested using the same database as that used for the decision performance test of the neural network according to the first embodiment of the present invention. For each hypothetical case, each participant, as a decision maker, was allowed one minute to review the 20 clinical and radiographic descriptors and select the most likely diagnosis from the 9 possible options of interstitial lung diseases. The decision maker was required to indicate the level of confidence for each disease, using a rating scale from 1 to 5, 5 being the highest level of confidence for positive decisions. This rating method used is the same as that used for ROC analysis.

Decision Performance Test

Figure 8:
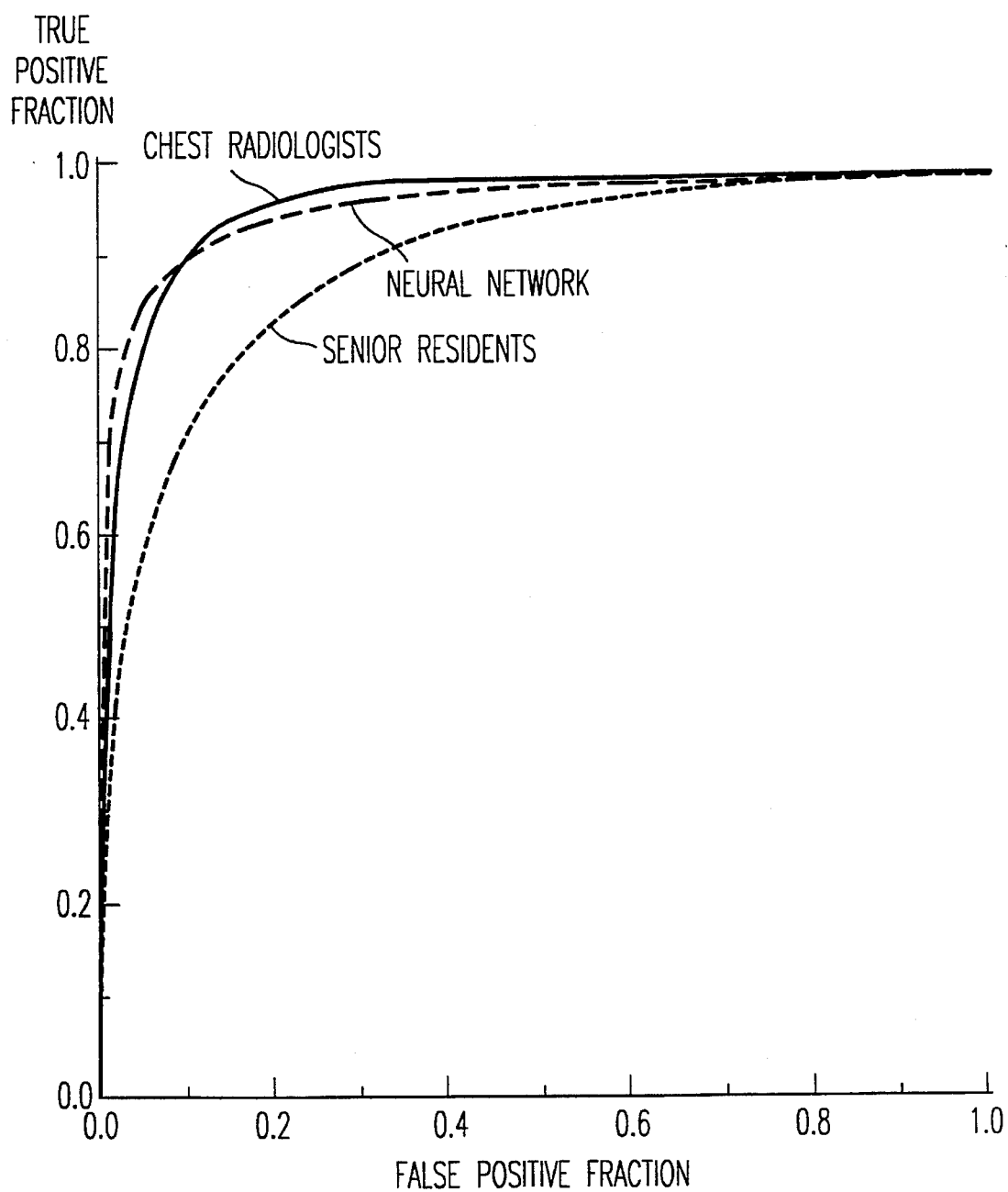
FIG. 8 is a graphical illustration comparing ROC curves of chest radiologists, senior radiology residents and the neural network according to the present invention indicating their decision performance and differential diagnosis of interstitial lung diseases.

The ROC curves of chest radiologists, senior radiology residents and the neural network for decision performance in differential diagnosis of interstitial lung diseases are shown in FIG. 8. The ROC curve of the neural network was comparable to the average ROC curve of the chest radiologist and superior to the average ROC curve of the senior radiology residents. The area under the ROC curves (Az), shown in FIG. 8, was 0.967 for both the chest radiologists and the neural network, and 0.905 for the senior residents.

The above results indicate that a neural network can be helpful to less expert observers, such as the senior radiology residents or clinicians, to bring their decision performance to a level closer to that of chest radiologists in the differential diagnosis of interstitial lung diseases.

As stated previously, there is some flexibility in designing the structure and the combination of neural networks to solve a problem. If a neural network has multiple output units, it can be replaced with an equal multiple of parallel neural networks that have the same number of input units but have only one output unit. According to a second embodiment of the present invention, 9 different neural networks each having 20 input units and one output unit corresponding to the 9 chosen diseases, respectively, can be designed.

Figure 9:
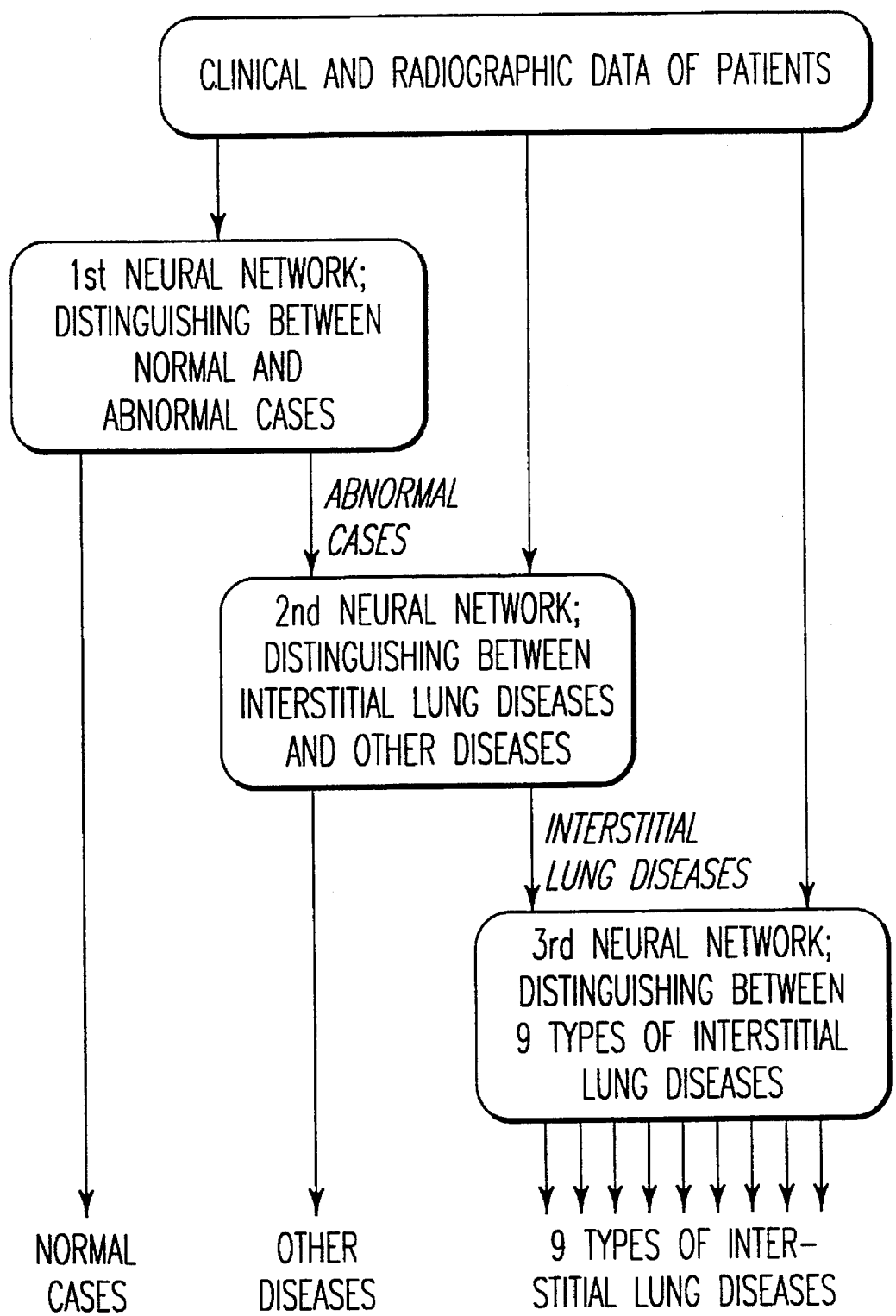
FIG. 9 is a block diagram of a second embodiment of the present invention illustrating three successive neural networks designed for differential diagnosis of interstitial lung diseases.

Alternatively, if a given problem can be divided into a series of smaller parts, the problem can be solved by using a series of neural networks. In a third embodiment of the present invention, as illustrated in FIG. 9, three successive neural networks are applied to the problem for differential diagnosis of interstitial lung diseases. The first neural network distinguishes between normal and abnormal patterns. The second neural network distinguishes between interstitial diseases and other diseases. Finally, the third neural network distinguishes among 9 types of interstitial lung diseases. It should be noted that another neural network can be added to this system to distinguish among other diseases such as primary lung cancer, pneumococcal pneumonia, pulmonary embolism, mediastinal tumor, etc. These parallel and serial approaches and combinations thereof, allow the solving of a large scale problem using multiple neural networks having rather small scale and simple structure.

In some cases, which occurs quite commonly in practical situations, it is not possible to acquire a complete set of input data. A method to obtain the output from the neural network even in the case of lack of some of the input information is to prepare several neural networks that have different numbers of input units corresponding to all possible combinations of missing data. According to a fourth embodiment of the present invention, in the differential diagnosis of interstitial lung diseases, for example, four of the 20 clinical data inputs (duration of symptoms, severity of symptoms, temperature and immune status) are sometimes unavailable. Thus, 16 different neural networks can be produced: one neural network having 20 inputs, four having 19 inputs, six having 18 inputs, four having 17 inputs, and one having 16 inputs, which represent all possible permutations of the four missing clinical data inputs. By training these 16 neural networks with a given complete set of initial input data, neural networks allowing the entry of an incomplete set of data are obtained.

Figure 10:
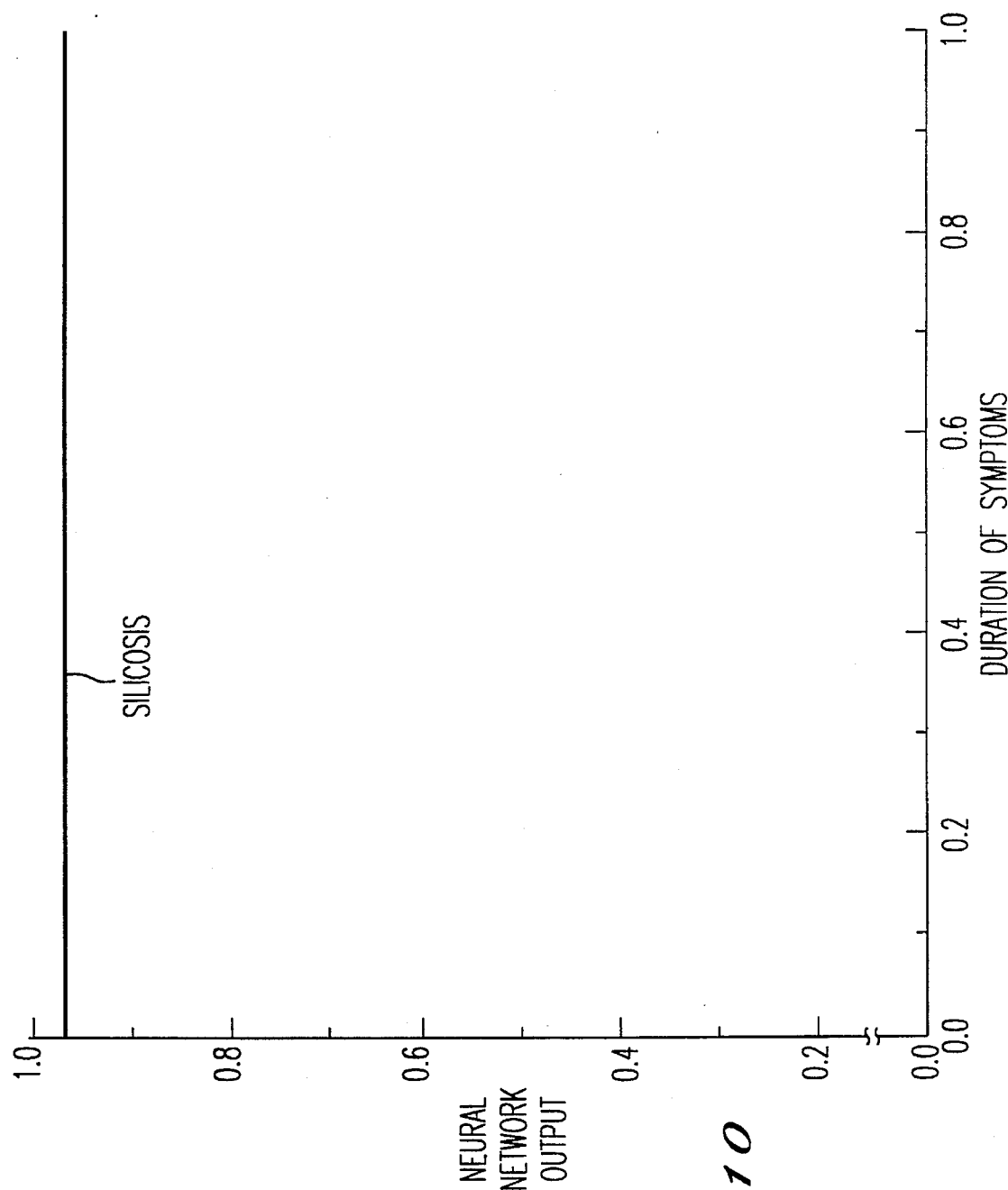
FIG. 10 is a graphical illustration of neural network output values at an output unit corresponding to silicosis for a range of dummy input values from 0 to 1 at an input corresponding to duration of symptoms.

A second method for handling an incomplete data set for testing is to run the neural network, which was trained with the incomplete data set, by entering "dummy" input values ranging from 0 to 1 with an appropriate increment such as 0.1 to an input unit in which the actual input data are missing. This method provides a range of output values at each unit with which the potential outcome for a case with the incomplete data set can be assessed by considering the possible variation of the missing input data. For example, if missing clinical data might not be essential for a certain disease, the output values at all output units would be basically unchanged for various dummy input values entered at the input unit which does not have the actual input data, as illustrated for silicosis in FIG. 10. The output value for the neural network in this case is not effected by the duration of symptoms.

Figure 11:
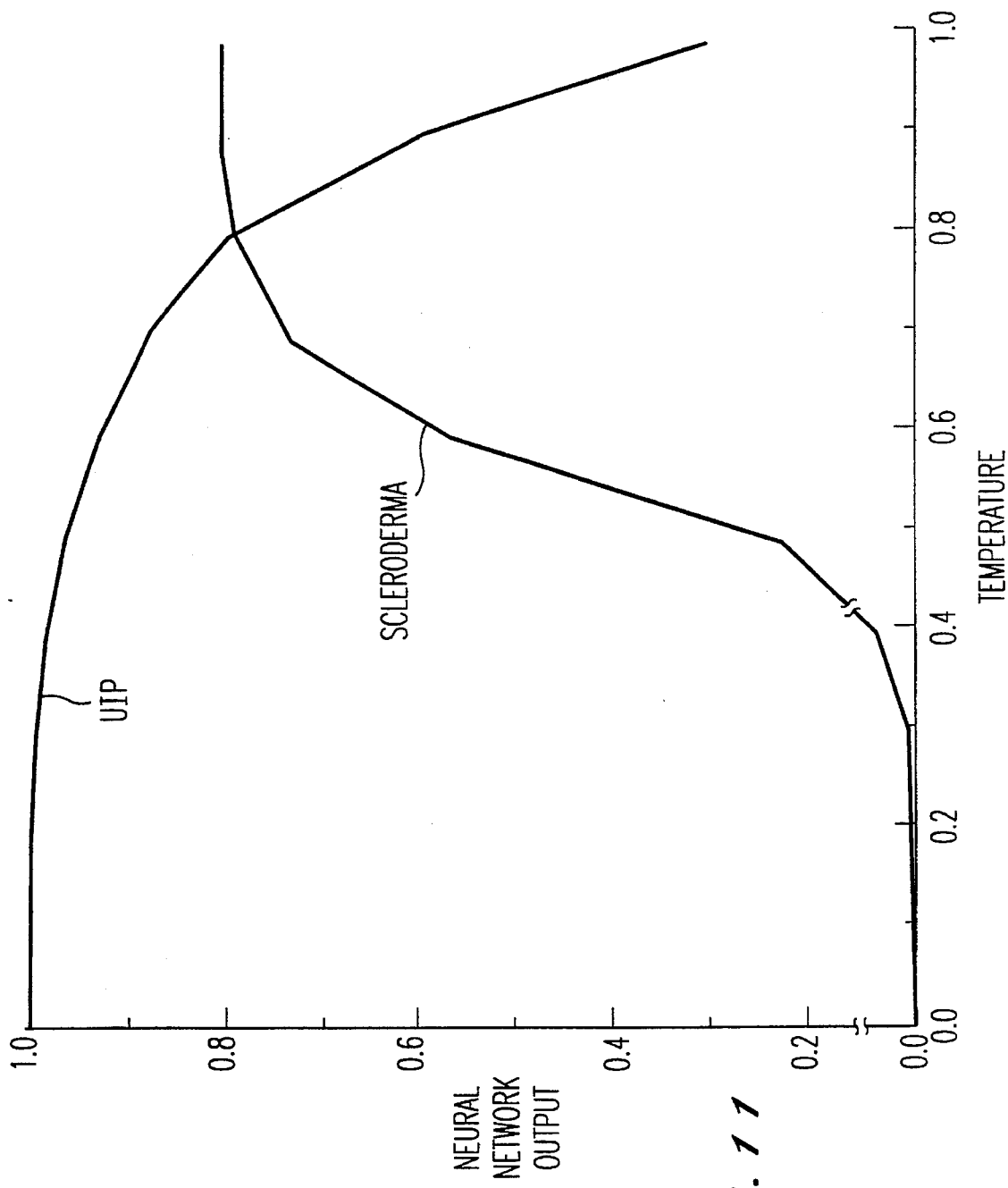
FIG. 11 is a graphical illustration of neural network output values at two output units corresponding to UIP and scleroderma for a range of dummy input values from 0 to 1 at an input unit corresponding to body temperature.

However, if the output values at some output units would be significantly changed for various dummy input values entered, the potential outcome leading to a certain disease or other diseases can be identified with the corresponding potential input values as illustrated in FIG. 11. In FIG. 11, the output of the neural network for UIP and scleroderma are shown as a function of body temperature. Here, if the body temperature is low, the disease is very likely to be UIP. However, if the body temperature is high, then the probability of the UIP decreases and the disease is very likely to be scleroderma. Thus, physicians would be able to provide differential diagnosis of the various lung diseases depending on the potential value of missing clinical data.

In other situations, an incomplete set of input data, which may be clinically important, may be desired or required to be entered into the training of the neural network. Here, it is assumed that the majority of the input data are available for all input units, namely, most data are the complete sets of input data. However, a small fraction of input data is assumed to be incomplete sets of input data. In such cases, the incomplete set of input data can be used for training the neural network by creating "dummy" values for missing input data which are obtained from the range of input values belonging to the same disease in the complete set of input data. The range and the distribution of "dummy" input values at the missing input unit will be, therefore, comparable to those actual input values at the same input unit. In other words, for the training of the neural network which generally includes a large number of iterations, such as 200, different dummy input values sampled for the actual distribution described above are chosen for every entry of the training.

The radiographic input data for the neural networks according to the invention are represented by numerical values which are estimated subjectively by a radiologist. This method may be impractical in many clinical situations. However, numerical values can be obtained from computerized automated analysis of lung texture, as disclosed in U.S. Pat. Nos. 4,839,807 and 4,851,484. Therefore, in a sixth embodiment of the present invention, a neural network is interfaced to a computerized scheme which performs automated lung texture analysis so that all radiographic input data to the neural network could be supplied in an objective and automated manner.

The present invention is not limited to exclusively that of differential diagnosis of interstitial lung diseases. For example, a neural network could be used in other areas of medical decision making, such as discrimination between benign and malignant patterns in mammography, which depend on simultaneous correlation of multiple clinical, laboratory and/or radiological findings.

Figure 13:
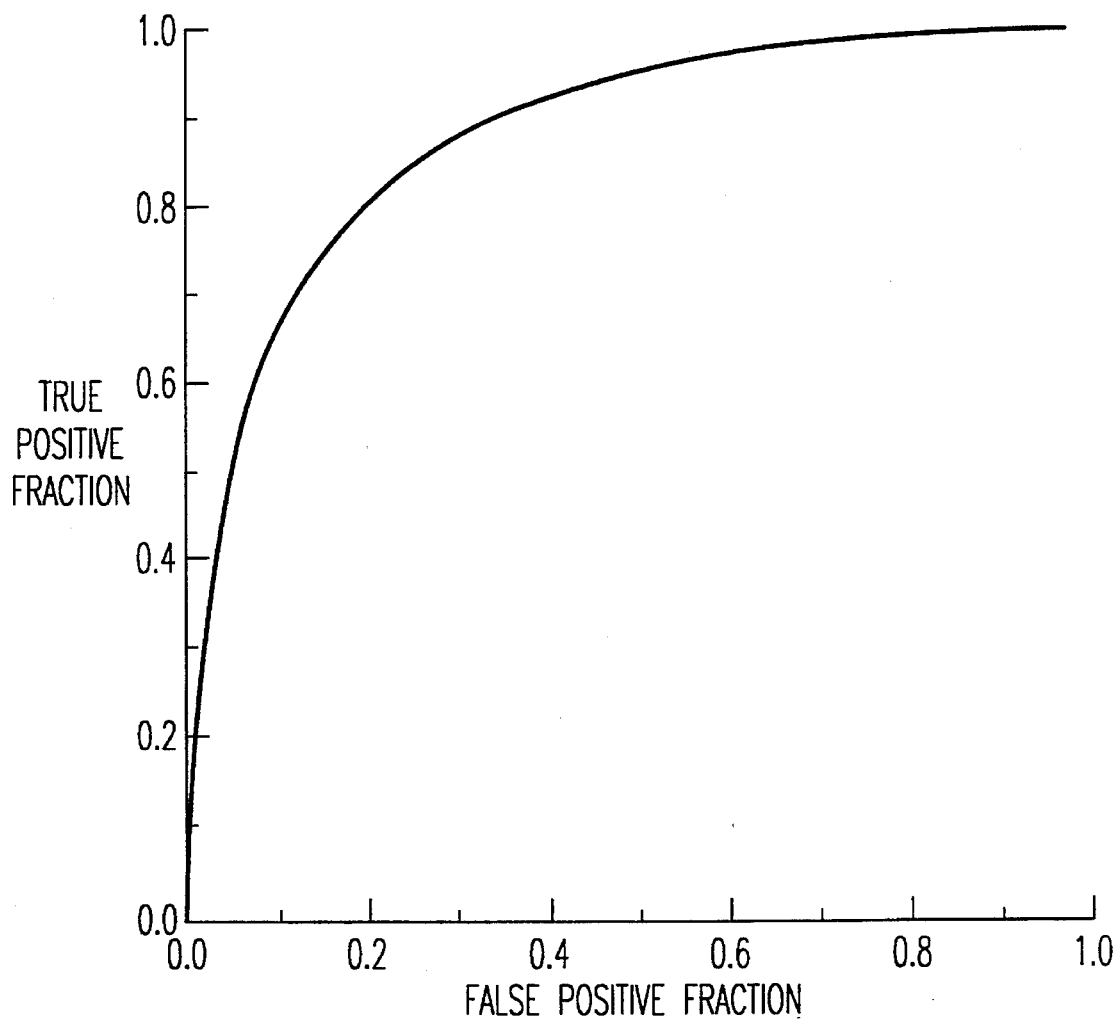
FIG. 13 is a graphical illustration of the ROC curve for a neural network according to a seventh embodiment of the present invention.

The neural network was applied to the mammographic diagnosis of breast cancer to distinguish between benign and malignant mammographic cases in a seventh embodiment. The network consists of a 3-layer feed-forward neural network with the back-propagating algorithm. The neural network has 45 input units, 1–25 hidden units and 1–5 output units. The neural network was trained by inputting ratings from mammographic features and clinical data from various cases, along with the corresponding correct benign/ malignant diagnosis. FIG. 12 lists the various input data including clinical parameters and radiographic descriptors. In the training process, for each case in a database of 60 cases selected from a textbook on mammography (Laszlo Tabar and Peter B. Dean, Teaching Atlas of Mammography, Georg Yhieme Verlag, (1985)), an expert mammographer rated each feature shown in FIG. 12. For example, if an abnormal mass density was observed, then the mammographer provided a rating from 0 to 10 regarding the shape of the density, as shown in II.B.1 of FIG. 12, with 0 corresponding to a linear one-dimensional feature, 5 being an oblong lesion and 10 corresponding to a generally spherical lesion. In addition, as shown in FIG. 12, the mammographer checked the correct diagnosis (malignant or benign), as well as the course of action he would advise in an actual clinical situation, which corresponded to desired outputs. These ratings were converted to values between 0 and 1, and were used as the inputs to, and desired outputs from, the neural network. ROC analysis was used in evaluating the mammography network using round robin and jackknife methods. With the database of 60 cases representing a range of benign and malignant cases, ROC analysis yielded an $A_z$ of approximately 0.85 to 0.9, as shown in FIG. 13. The high value of $A_z$ indicates the high degree accuracy for mammographic diagnosis possible using neural networks.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for differential diagnosis of a plurality of predetermined interstitial lung diseases, comprising:

selecting a plurality of clinical parameters defining characteristics of a subject;

selecting a plurality of radiographic descriptors comprised of predetermined features obtained from a radiographic chest image defining interstitial lung diseases characteristics;

converting said plurality of clinical parameters and said plurality of radiographic descriptors into numerical expressions;

transforming each of said numerical expressions into a number in a predetermined range;

inputting said transformed numerical expressions into a plurality of successive neural networks; and diagnosing at least one of said plurality of interstitial lung diseases using said neural networks in accordance with said input expressions including:

distinguishing between normal and abnormal patterns in said radiographic chest image using a first of said plurality of successive neural networks;

distinguishing between said plurality of predetermined interstitial lung diseases and other diseases using a second of said plurality of successive neural networks; and distinguishing between said plurality of predetermined interstitial lung diseases using a third of said plurality of successive neural networks.

2. A method for differential diagnosis of a plurality of interstitial lung diseases using an incomplete set of input data, comprising:

selecting a plurality of clinical parameters defining characteristics of a subject;

selecting a plurality of radiographic descriptors comprised of predetermined features obtained from a radiographic chest image defining characteristics of interstitial lung diseases;

forming a complete set of input data comprised by said plurality of clinical parameters and said plurality of radiographic descriptors;

converting said plurality of clinical parameters and said plurality of radiographic descriptors into numerical expressions;

transforming each of said numerical expressions into a number in a predetermined range;

training a neural network comprising a plurality of successive neural networks to identify each of said plurality of interstitial lung diseases using a database of said complete set of data;

inputting said transformed numerical expressions into said neural network, said input expressions representing incomplete sets of input data; and diagnosing at least one of said plurality of interstitial lung diseases using said neural network in accordance with said input expressions, including:

distinguishing between normal and abnormal patterns in said radiological chest image using a first of said plurality of successive neural networks;

distinguishing between said plurality of predetermined interstitial lung diseases and other diseases using a second of said plurality of successive neural networks; and distinguishing between said plurality of predetermined interstitial lung diseases using a third of said plurality of successive neural networks.

3. A method for differential diagnosis of a plurality of predetermined interstitial lung diseases using an incomplete set of input data, comprising:

selecting a plurality of clinical parameters defining characteristics of a subject;

selecting a plurality of radiographic descriptors comprised of predetermined features obtained from a radiographic chest image defining characteristics of interstitial lung diseases, including at least plural of the following fourteen radiographic descriptors:
distribution of infiltrates in 6 lung zones,
homogeneity, fineness, nodularity, septal lines and honeycombing of said infiltrates, and
lymphadenopathy, pleural effusions and heart size;

forming a complete set of input data comprised by said plurality of clinical parameters and said plurality of radiographic descriptors;

converting said plurality of clinical parameters and said plurality of radiographic descriptors into numerical expressions;

transforming each of said numerical expressions into a number in a predetermined range;

training a neural network comprising a plurality of successive neural networks to identify each of said plurality of predetermined interstitial lung diseases using a database of said complete set of data;

inputting said transformed numerical expressions into said neural network, said input expressions representing incomplete sets of input data;

diagnosing at least one of said plurality of predetermined interstitial lung diseases using said neural network in accordance with said input expressions;

distinguishing between normal and abnormal patterns in said radiographic chest image using a first of said plurality of successive neural networks;

distinguishing between said plurality of predetermined interstitial lung diseases and other diseases using a second of said plurality of successive neural networks; and distinguishing between said plurality of predetermined interstitial lung diseases using a third of said plurality of successive neural networks.

* * * * *